United States Patent [19]

Fankhauser et al.

[11] Patent Number: 4,913,905
[45] Date of Patent: Apr. 3, 1990

[54] TRANSDERMAL THERAPEUTIC SYSTEMS FOR ACTIVE INGREDIENT COMBINATIONS

[75] Inventors: Peter Fankhauser, Ettingen; Lotte Schenkel, Basle, both of Switzerland

[73] Assignee: Ciba-Geigy Corporation, Ardsley, N.Y.

[21] Appl. No.: 172,883

[22] Filed: Mar. 25, 1988

[30] Foreign Application Priority Data

Apr. 2, 1987 [CH] Switzerland ............... 1259/87

[51] Int. Cl.$^4$ .............................................. A61L 15/03
[52] U.S. Cl. ..................................... 424/449; 424/447
[58] Field of Search ................................ 424/447–449

[56] References Cited

U.S. PATENT DOCUMENTS

| 3,968,245 | 7/1976 | Higuchi | 424/330 |
| 4,379,454 | 4/1983 | Campbell et al. | 604/897 |
| 4,695,465 | 9/1987 | Kigasawa et al. | 424/447 |
| 4,816,258 | 3/1989 | Nedberge et al. | 424/448 |

FOREIGN PATENT DOCUMENTS 136011 4/1985 European Pat. Off. .
196769 10/1986 European Pat. Off. .
2093694 6/1985 United Kingdom .

OTHER PUBLICATIONS

Keller, Rundschau Med. (PRAXIS) vol. 75 No. 12 (1986).
Schröder et al, Pharma Chemie, G. Thieme, Stuttgart (1982).

Primary Examiner—Nancy A. B. Swisher
Attorney, Agent, or Firm—JoAnn Villamizar

[57] ABSTRACT

The present invention relates to a transdermal therapeutic system for the combined administration of oestrogens and gestagens. The therapeutic system consists of:
(1) a closed outer layer which is impermeable to the constituents of the active ingredient formulation,
(2) a reservoir containing essential constitutents of the active ingredient formulation and, optionally, a membrane,
(3) an adhesive layer and
(4) a peel-off protective layer on the adhesive layer.

The system contains an oestrogen derivative in combination with a synthetic gestagen, and an agent that enhances percutaneous absorption.

3 Claims, No Drawings

TRANSDERMAL THERAPEUTIC SYSTEMS FOR ACTIVE INGREDIENT COMBINATIONS

The present invention relates to a therapeutic system for the transdermal combined administration of oestrogens and gestagens, to processes for the preparation of this system and to the use of oestrogens and gestagens in transdermal therapeutic systems for the treatment of the climacteric syndrome.

The climacteric syndrome comprises all the withdrawal symptoms occurring after the menopause, which are caused by so-called oestrogen deficiency. Oestrogen replacement, which has been known for a long time, is prophylactically and therapeutically significant. A favourable effect on hot flushes, sleep disorders and dysphoria is achieved An important factor is the reduction in morbidity and mortality resulting from fractures which are due to osteoporosis and from coronary and cerebrovascular diseases; see, in this connection, P. J. Keller, Schweiz. Rundschau Med. (Praxis) 75, No. 12 (1986), page 328.

When oestrogens, for example $17\beta$-oestradiol, are administered orally, their resorption is unsatisfactory owing to their low water-solubility following oral administration. The rapid metabolisation of $17\beta$-oestradiol by the liver necessitates a high dosage which results in the frequent occurrence of undesirable side-effects, inter alia nausea, thromboembolism, etc; see, in this connection, Pharm. Chemie, E. Schröder et al., G. Thieme, Stuttgart 1982, page 571.

In long-term treatment with oestrogens that are not combined with gestagens, hyperplasia of the endometrium may, in addition, occur which increases the risk of tumours.

Numerous studies in the USA have postulated a 3.3 to 6 times higher incidence of endometrium carcinomas following treatment with conjugated oestrogens, oestradiol or oestradiol valerate. A link between increased oestrogen levels and the incidence of breast carcinoma is also thought likely.

In order to avoid such risks, especially the risk of carcinoma of the endometrium and the breast, and also thromboembolic complications, P. J. Keller (loc. cit.) recommends transdermal administration of oestrogens such as $17\beta$-oestradiol, in particular the use of transdermal therapeutic systems containing that active ingredient and supplementation of the treatment by gestagens. Up to now, however, only oral combined preparations have been available for such combined administration. There is therefore a need for transdermal combined preparations containing oestrogens and gestagens, especially transdermal therapeutic systems containing that combination of active ingredients.

DE-A No. 3 205 258 describes therapeutic systems in the form of plasters by means of which oestradiol can be applied transdermally with the aid of an agent that enhances percutaneous absorption, such as ethanol. The advantage of such systems resides in the lower dosage of oestradiol when the liver "first pass" effect is avoided, so that, with this form of administration, the metabolisation of relatively large quantities of active ingredient does not occur.

Hitherto, no suitable transdermal therapeutic systems have been available for the administration of natural and synthetic gestagens. Thus, even when using the vehicle described in DE-A No. 3 205 258, for example ethanol gel, the amount of the natural gestagen derivative progesterone that passes through the skin is not sufficient to achieve an adequate therapeutic effect when using transdermal therapeutic systems of acceptable size.

It has now surprisingly been found that the flux of synthetic gestagens such as norethisterone acetate when using a suitable vehicle is sufficient for a therapeutic effect using transdermal systems of conventional size (about 5 to 25 $cm^2$), so that the minimum amounts of gestagen necessary for a therapeutic effect can be supplied transdermally.

This surprising discovery can be used to achieve the object underlying this invention which is to produce a suitable transdermal therapeutic system containing an oestrogen, such as $17\beta$-oestradiol, combined with a gestagen.

The present invention relates to multi-layered therapeutic systems for the transdermal administration of oestrogens and gestagens, consisting of:

(1) a closed outer layer which is impermeable to the constituents of the active ingredient formulation, (2) a reservoir containing essential constituents of the active ingredient formulation and, optionally, a membrane, (3) an adhesive layer and (4) a peel-off protective layer on the adhesive layer, characterised in that the active ingredient formulation contains an oestrogen derivative in combination with a synthetic gestagen derivative, and an agent that enhances percutaneous absorption (penetration enhancer).

The therapeutic system according to the invention for the transdermal administration of oestrogens and synthetic gestagens is preferably in the form of a plaster having a base surface that is at least as large in area as the area of skin envisaged for the administration and at least as large as is required for it to fit firmly over the entire period of treatment. The base surface must be large enough for sufficient quantities of the active constituents of the active ingredient formulation (active ingredient and the agent for enhancing percutaneous absorption, hereinafter "penetration enhancer") to be absorbed by the skin. Although, in theory, large areas of the skin are available for taking the plaster, for reasons of comfort the maximum surface area of the base surface of the plaster is about 200 $cm^2$.

The plaster may be of any geometrical shape, e.g. may be oval, elliptical, circular, rectangular, optionally with rounded corners, oblong or rectangular with one or two rounded tabs. Other shapes are also possible.

The outer layer (1) consists of a material or of a combination of materials that must be impermeable to the constituents of the formulation contained in the reservoir (2). It serves as a protecting and supporting layer. To produce the outer layer, it is possible to use high or low pressure polymers such as polyethylene, polypropylene, polyvinyl chloride, polyethylene terephthalate or also cellulose acetate or vinyl acetate/vinyl chloride copolymers and combinations, especially composite foils thereof. An impermeable, flexible outer layer that conforms to the shape of the part of the body to which the plaster is applied is preferred.

The reservoir (2) is situated between the outer layer (1) and the adhesive layer (3) and contains essential constituents of the active ingredient formulation, e.g. the active ingredients together with the penetration enhancer, or penetration enhancer alone. In addition, the reservoir may contain polymeric materials for the formation of a porous or permeable membrane.

The reservoir (2) can contain a liquid, semi-solid or solid active ingredient formulation which, for example, is in firm contact with the skin. Such an arrangement is known per se and is described, for example, in British Patent Application No. 2,021,950. The area of the outer layer (1) is greater than the area occupied by the reservoir (2) and, therefore, the outer layer projects beyond the reservoir, the projecting portion of the outer layer (1) being provided with the adhesive layer (3) and adhering to the skin. The peel-off protective layer (4) lies over the adhesive layer (3) and over the reservoir (2).

The reservoir (2) can also be in firm contact with the adhesive layer (3). In this case, the active ingredient combination may be present both in the reservoir and in the adhesive layer (3). Such an arrangement is described in U.S. Pat. No. 4,597,961. The outer layer (1) is also larger in area than the area occupied by the reservoir (2) and projects beyond the latter. The adhesive layer (3) covers both the reservoir (2) and the projecting portion of the outer layer (1). The peel-off protective layer (4) lies on top of the adhesive layer.

The reservoir (2) can also contain liquid polymeric material in which the active ingredient formulation or constituents thereof are homogeneously dispersed. Such polymeric materials are, for example, silicone rubber (silicones), e.g. linear organosiloxanes in which every silicon atom in the siloxane chain is substituted by two identical or different alkyl, e.g. methyl or ethyl, aryl, e.g. phenyl, alkenyl, e.g. vinyl or allyl, alkylaryl, e.g. tolyl or xylyl, or aralkyl, e.g. benzyl, radicals, and every terminal silicon atom is substituted by three of the mentioned organic radicals. The preparation of these silicones is described in U.S. Pat. Nos. 2,541,137, 2,723,966, 2,863,846, 2,890,188, 2,927,907, 3,002,951 and 3,035,016.

In addition to the liquid polymeric material and the active ingredient formulation, the reservoir (2) can also contain other liquids such as glycerol or propylene glycol and also water and have the release properties described in U.S. Pat. No. 4,291,015.

The contents of the reservoir (2) preferably consist exclusively of the actual active ingredient formulation which contains the penetration enhancer, especially ethanol, the active ingredient combination of an oestrogen with a synthetic gestagen and, optionally, further adjuvants, e.g. gelling agents.

The reservoir (2) can, in addition, be provided with a permeable layer of the required permeability to the active ingredient combination and the penetration enhancer. This layer controls the rate of release of the penetration enhancer, and optionally of the active ingredient combination, from the system to the skin and is also called a control or regulating membrane.

The materials that can be used in the therapeutic systems of the invention for producing the permeable layer are known per se. Such membrane materials may be homogeneous (diffusion membranes) or macrostructured (porous membranes). The latter may be in the form of a sponge-like structure having a skeleton of polymeric material with interconnected voids and pores dispersed therein. Membrane materials that control the rate of release may consist of isotropic material with a homogeneous structure or of anisotropic material with an inhomogeneous structure. Such materials are commercially available and can be produced in various ways, for example as described by R. E. Kesting, Synthetic Polymer Membranes, McGraw Hill, Chapters 4 and 5, 1971, J. D. Ferry, Ultrafiltration Membranes, Chemical Review, Vol. 18, page 373, 1984.

Membrane materials having from 5 to 95% by volume voids and an effective pore diameter of approximately from $1.0 \times 10^{-9}$ m to $1.0 \times 10^{-4}$ m are especially suitable. More especially suitable are membrane materials having pore diameters of less than approximately $5.0 \times 10^{-9}$ m and molecular diffusion. For best results, reference should be made to the prior art and the known embodiments with known membrane materials and known shapes which ensure an optimum rate of release of the active ingredient combination. In particular, the membrane material must be chemically resistant to the active ingredient combination and to the penetration enhancer used.

A list of suitable membrane materials, which should not be regarded as exhaustive, is given below:

polycarbonates, e.g. linear polyesters of carbonic acid derivatives that contain carbonate groups in the polymer chain and can be prepared, for example, by reacting dihydroxy aromatic compounds with phosgene. Such materials are obtainable from General Electric under the Trade Mark Lexan ®;

polyvinyl chlorides, e.g. PVC which is obtainable from Goodrich under the Trade Mark Geon ® 121;

polyamides of the polyhexamethyleneadipamide type, or polyamides known by the generic name "Nylon". An especially suitable material is sold under the Trade Mark Nomex ® by DuPont;

acrylic acid copolymers, e.g. those which are sold under the trade name Dynel ® and consist of about 60% polyvinyl chloride and 40% acrylonitrile, and styrene/acrylic acid copolymers and the like;

polysulphones with diphenylsulphone groups in the linear chain. Such polymers are sold as P-1700 by Union Carbide;

halogenated polymers such as polyvinylidene fluorides that are sold, for example, under the Trade Mark Kynar ® by Pennwalt; polyvinyl fluorides that are obtainable from DuPont under the Trade Mark Tedlar ®, and polyfluorohalocarbons obtainable under the Trade Mark Aclar ® from Allied Chemical;

polychloroethers that are sold by Hercules under the Trade Mark Penton ®, and other similar thermoplastic polymers;

acetal polymers such as the polyformaldehyde polymers that are sold by DuPont under the Trade Mark Delrin ®, and the like;

acrylic acid resins such as polymethyl methacrylate, poly-n-butyl methacrylate and the like;

polyethylene and copolymers of ethylene, e.g. with vinyl acetate or acrylates.

Other polymers such as polyurethanes, polyimides, polybenzimidazoles, polyvinyl acetate, aromatic and aliphatic polyethers, cellulose esters, for example cellulose triacetate, cellulose, Colledion ® (cellulose nitrate with 11% nitrogen), epoxy resins, polyolefins, e.g. polyethylene/polypropylene, porous rubber, polyvinylpolypyrrolidone, crosslinked polyvinyl alcohol, copolymers of vinylpyrrolidone and vinyl alcohols, polyelectrolyte structures consisting of two ionically associated polymers as are described in U.S. Pat. Nos. 3,549,016 and 3,546,142, polystyrene derivatives such as polystyrene sodium sulphonates or polyvinylbenzyltrimethylammonium chlorides, polyhydroxyethyl methacrylates, polyisobutyl vinyl ether and similar polymers can also be used. Other copolymers that are obtainable by copolymerisation of various amounts of the monomers forming the basis of the mentioned polymers can also be used to produce the membrane material which determines the rate of release of the penetration enhancer.

When using a permeable membrane, several arrangements are possible: the active ingredient formulation is arranged between the outer layer (1) and the membrane layer. In this arrangement, the outer layer and the membrane form a volume which can optionally be divided into several compartments. In certain embodiments, the outer layer (1) and the membrane layer are joined, e.g. welded or glued, to each other at the very edge. In these embodiments, the active ingredient combination and the penetration enhancer are held in the same reservoir. These embodiments are preferred when the active ingredient formulation is liquid or semi-solid.

It is also possible, in accordance with the embodiment described in German Offenlegungsschrift No. 3 205 258, to fill the volume formed by the outer layer (1) and the membrane only with penetration enhancer, e.g. ethanol, and optionally with a gelling agent such as gelatin, and to apply the active ingredient combination to the other side of the membrane. In this case, the membrane would control only the rate of diffusion of the enhancer. The active ingredient combination can be arranged in a separate layer between membrane and adhesive layer (4) and optionally or exclusively in the adhesive layer (4).

The reservoir (2) can, in addition, be divided into several compartments. This division into compartments is suitable for liquid active ingredient formulations and prevents the latter from sinking and becoming concentrated at the lowest point of the system if cavities or folds are formed as a result of the plaster not being stored flat. Division into compartments is especially advantageous if the reservoir layer occupies an area of more than 30 cm². The compartments can be distributed as desired. For example, a radial arrangement of the partitions, extending from the middle point of the plaster, or vertical or horizontal boundaries, or oblique lines etc. are possible.

Division of the compartments, especially by partition material or seal seams, can be effected by hot-welding. In this procedure, the material of the outer layer (1) is welded to the material of the membrane layer.

The adhesives that can be used in dermatology are suitable for the adhesive layer (3). Suitable adhesives are, for example, adhesive formulations of acrylic acid resins or methacrylic acid resins, e.g. polymers of acrylic acid or methacrylic acid esterified by alcohols such as n-butanol, n-pentanol, isopentanol, 2-methylbutanol, 1-methylbutanol, 1-methylpentanol, 2-methylpentanol or 3-methylpentanol, 2-ethylbutanol, isooctanol, n-decanol or n-dodecanol, or copolymers of these acrylic acid or methacrylic acid esters with monomers containing ethylene groups, such as acrylic acid itself, methacrylic acid, acrylamide, methacrylamide, N-alkoxymethacrylamide, N-alkoxymethylmethacrylamide, N-tert.-butylamide, itaconic acid, vinyl acetate, N-branched alkylmaleic acid amide in which the branched alkyl group has from 10 to 24 carbon atoms, glycol diacrylates or mixtures thereof, natural or synthetic rubber such as styrenebutadiene, butyl ether, neoprene, polyisobutylene, polybutadiene and polyisoprene, polyvinyl acetate, urea formaldehyde resins, resorcinol formaldehyde resins, cellulose derivatives such as ethylcellulose, methylcellulose, nitrocellulose, cellulose acetate butyrate and carboxymethylcellulose, and also natural gums such as guar, acacia, pectin, starch, dextrin, albumin, gelatin, casein et.. Thickeners and stabilisers may also be added to the adhesives mentioned.

The adhesive layer (3) may be applied to some or all of the membrane. If the membrane is completely covered by adhesive layer (3) the latter may, in addition to its actual function as an adhesive to the skin, act as a permeable membrane. The desired membrane properties, e.g. control of the rate of diffusion of the penetration enhancer, can be obtained by varying the thickness and composition of the adhesive layer. The adhesive layer (3) may, in addition, contain the total amount, or preferably a proportion of, the active ingredient combination of oestrogens and gestagens. The amount of active ingredient contained in the adhesive layer can be used, in particular, to administer an initial surge dose before the continuous release, which is controlled by the therapeutic system, commences at the desired therapeutic level.

The membrane can also be covered by the adhesive layer (3) partially and/or discontinuously. A covering at the edges is possible, for example an annular circumferential covering. The membrane can also be covered in a pattern, for example in a rhomboidal pattern. The membrane can be covered at the outer edge by a continuous band of adhesive material, for example in the shape of a ring, and on the inside surface with discontinuous bands, for example in a rhomboidal pattern.

The protective layer (4) is removed before application. It consists of materials that are impermeable to the constituents of the reservoir layer (2). It is possible to use the same materials as those used for producing the outer layer (1), and also metal foils, for example thin aluminium foils. Organic polymers are rendered capable of being peeled off the adhesive layer (3) by suitable surface treatment, for example silicone treatment.

The active ingredient formulation contained in the transdermal therapeutic system of the invention, especially in the reservoir (2), contains as adjuvant an agent that enhances percutaneous absorption (penetration enhancer) which increases the flux of the active ingredient combination of oestrogens and synthetic gestagens through the skin, so that a greater quantity of active ingredients can be absorbed by the skin per unit of application area and per unit of time. The penetration enhancer can, in addition, accelerate the flow of the active ingredients through the permeable membrane layer in membrane systems In particular, the use of a suitable penetration enhancer results in the administration through the skin of that dosage of active ingredients which is required per unit of time to maintain the therapeutic level Suitable penetration enhancers have a higher flux through the skin than do the active ingredients whose absorption is to be enhanced and can be mixed with other pharmaceutically acceptable adjuvants.

Suitable penetration enhancers (flux enhancers) are preferably monovalent, saturated or unsaturated aliphatic, cycloaliphatic or aromatic alcohols having from 4 to 12 carbon atoms, e.g. n-hexanol or cyclohexanol, aliphatic, cycloaliphatic or aromatic hydrocarbons having from 5 to 12 carbon atoms, e.g. hexane, cyclohexane, isopropylbenzene and the like, cycloaliphatic or aromatic aldehydes and ketones having from 4 to 10 carbon atoms, such as cyclohexanone, acetamide, N,N-di-lower alkylacetamides such as N,N-dimethylacetamide or N,N-diethylacetamide, $C_{10}$–$C_{20}$-alkanoylamides, e.g. N,N-dimethyllauroylamide, 1-n-$C_{10}$–$C_{20}$-alkylazacycloheptan-2-one, e.g. 1-n-dodecylazacycloheptan-2-one (Azone®, Nelson), or N-2-hydroxyethylacetamide, and known vehicles and/or penetration enhancers such as aliphatic, cycloaliphatic and aromatic esters, N,N-di-lower alkylsulphoxides, unsaturated oils, halogenated or nitrated aliphatic or cycloaliphatic hydrocarbons, salicylates, polyalkylene glycol silicates, and mixtures thereof.

$C_2$–$C_4$-alkanols, e.g. isopropanol or isobutanol and, especially, ethanol, are especially preferred as penetration enhancers.

The amount of active ingredient, present in the therapeutic system, that is required to achieve a therapeutic effect depends on many factors: inter alia the minimum necessary dosage, the permeability of the membrane material, which determines the flux, and of the adhesive layer, and the period for which the plaster will be fixed to the skin or the mucous membranes. Since the active ingredient is to be released over a period of more than one day, there is, in fact, no upper limit to the maximum amounts of active ingredient present in the plaster. The minimum amount of active ingredient is determined by the requirement that sufficient quantities of active ingredient must be present in the plaster to maintain the desired rate of release over the given period.

The therapeutic system of the invention contains an active ingredient combination of oestrogens with synthetic gestagens.

The term "oestrogens" comprises both the natural 17β-oestradiol and the semi-synthetic oestrogen derivatives such as the esters of natural oestrogen, for example estradiol-17-oenanthate, estradiol-17-valerate, estradiol-3-benzoate, estradiol-17-undecenoate, estradiol-16,17-dihemisuccinate or estradiol-17-cypionate, 17-alkylated oestrogens, e.g. ethinylestradiol, ethinylestradiol-3-isopropylsulphonate, quinestrol, mestranol or methylestradiol, and non-steroidal compounds having oestrogen activity, e.g. diethylstilbestrol, dienestrol, clomifen, chlorotrianisen or cyclofenil.

The term "synthetic gestagens" comprises derivatives of natural progesterone, dydroprogesterone or medrogesterone, e.g. 17α-hydroxyprogesterone derivatives, e.g. hydroxyprogesterone acetate, medroxyprogesterone acetate, megestrol acetate, chlormadinone acetate, dihydroxyprogesterone-16,17-acetophenonide or cyproterone acetate, 17α-hydroxy-19-progesterone derivatives, e.g. gestonorone caproate, and, especially, 19-nortestosterone derivatives, e.g. norethisterone, norethisterone-17-oenanthate, norethisterone-17-acetate, norethynodrel, ethynodiol-3,17-diacetate, lynestrenol, quingestanol-17-acetate, norgestrienone, norgestrel, levonorgestrel, hydroxyprogesterone caproate, allylestrenol or methylestrenolone.

The active ingredient combination of oestrogens with synthetic gestagens contains, as oestrogen component, preferably 17β-oestradiol or an oestrogen conjugate, e.g. 17β-oestradiol and estradiol-17-valerate, and, as synthetic gestagen component, preferably a nortestosterone derivative, e.g. norgestrel or norethisterone-17-acetate.

The active ingredient combination consists most especially of 17β-oestradiol and norethisterone-17-acetate.

The active ingredient combination present in the therapeutic system of the invention has the advantage that it permits the combined dermal administration of oestrogens and gestagens. This form of administration is advantageous by virtue of, in particular, its simplification of the mode of administration in comparison with a combination of transdermal and oral administration, and by virtue of its avoidance of the liver "first pass" effect, so that lower dosages can be employed than in the case of peroral administration which has been customary hitherto.

The therapeutic system of the invention contains, for example, approximately from 0.2 to 20 mg of 17β-oestradiol and approximately from 0.5 to 60 mg of norethisterone-17-acetate. Preferred dosage forms contain approximately from 2.0 to 5.0 mg of 17β-oestradiol and approximately from 5.0 to 30 mg of norethisterone-17-acetate. These amounts are sufficient to ensure the release and absorption of minimum daily therapeutic amounts of approximately 0.05 mg of 17β-oestradiol and approximately 0.2 mg of norethisterone-17-acetate even when the plaster is worn for several days.

Adjuvants can be added to the active ingredient combination. Suitable adjuvants are water, isotonic aqueous sodium chloride solution, dextrose in water or sodium chloride solution, liquid glyceryl triesters with low molecular weight fatty acids, lower alkanols, natural oils such as corn oil, groundnut oil, sesame oil, castor oil or condensation products thereof with ethylene oxide, and the like, hydrocarbons such as pharmaceutical grade mineral oil, silicones, emulsifiers such as mono-glycerides or diglycerides of fatty acids, phospholipic acid derivatives such as lecithin or cephalin, polyalkylene glycols such as polyethylene glycol, aqueous phases to which a swelling agent such as sodium carboxymethylcellulose, sodium alginate, polyvinylpolypyrrolidone, etc. has been added and to which, in addition, dispersion agents or emulsifiers such as lecithin may be added, polyoxyethylene and the like. The adjuvants may, in addition, contain additives such as preservatives, stabilisers, wetting agents, emulsifiers, etc.

If $C_2$–$C_4$-alkanols such as ethanol are used as penetration enhancers, gelling agents such as gelatin or swelling agents such as cellulose ethers, e.g. hydroxypropylcellulose, are preferably added as adjuvants to the active ingredient formulation.

The present invention relates preferably to multilayered therapeutic systems for the transdermal administration of oestrogens and gestagens, consisting of:

(1) a closed outer layer which is impermeable to the constituents of the active ingredient formulation, (2) a reservoir containing essential constituents of the active ingredient formulation and, optionally, a membrane, (3) an adhesive layer and (4) a peel-off protective layer on the adhesive layer, characterised in that the active ingredient formulation contains an oestrogen derivative in combination with a synthetic gestagen derivative, and ethanol as an agent that enhances percutaneous absorption.

The present invention relates especially to multilayered therapeutic systems in the form of plasters for the transdermal administration of oestrogens and gestagens, consisting of:

(1) a closed outer layer which is impermeable to the constituents of the active ingredient formulation, (2) a reservoir containing essential constituents of the active ingredient formulation and a permeable membrane layer, (3) an adhesive layer and (4) a peel-off protective layer on the adhesive layer, characterised in that the active ingredient formulation contains 17β-oestradiol in combination with norethister-one-17-acetate, and ethanol as an agent that enhances percutaneous absorption.

The transdermal therapeutic systems of the invention are prepared in a manner known per se, for example as follows: The adhesive layer (3) is applied to a base layer (peel-off protective layer (4)), e.g. foil or film. The constituents of the active ingredient reservoir, for example membrane layer and active ingredient formulation, can also be applied to the base layer, and the impermeable outer layer can be placed on top. The plaster is then punched out of the master. The reservoir is optionally bonded to the outer layer with additional adhesive. The reservoir can also be hot-welded to the membrane layer or to the adhesive layer. In liquid-filled systems, the membrane layer is applied to the adhesive layer (3) and the active ingredient formulation is placed on the membrane.

The preparation processes are described in U.S. Pat. No. 3,797,494, preferably in DE-A No. 26 04 718 and DE-A No. 32 05 258 and in U.S. Pat. Nos. 4,031,894 and 4,262,003 or in the publication by H. Asche in Schweiz. Rundschau Med. (Praxis) 74, No. 11, 257-260 (1985), but the use of these processes according to the invention is not limited to the transdermal therapeutic systems described in those publications. The preferred transdermal therapeutic system described in DE-A No. 32 05 258 is a therapeutic system in the form of a plaster-like patch that releases the active ingredient combination transdermally, avoiding side-effects, in a quantity of from 0.3 to 15 μg/hour and delivers it through the skin so that the active ingredient content of the plasma remains approximately constant.

The transdermal therapeutic system of the invention is suitable for the administration of the active ingredient combination of oestrogens and synthetic gestagens in the treatment of all conditions caused by oestradiol deficiency, for example osteoporosis, headaches, nausea, depression, hot flushes, etc., especially symptoms referred to collectively as the "climacteric syndrome".

The transdermal therapeutic system of the invention is suitable, in addition, for the cyclically intermittent treatment of the climacteric syndrome, in which, for example, transdermal therapeutic systems containing 17β-oestradiol as active ingredient, for example the Estraderm ®-TTS system (Ciba-Geigy), are applied for two, or preferably three, weeks and then the transdermal therapeutic system of the invention containing the active ingredient combination of 17β-oestradiol and norethisterone-17-acetate is used for two weeks or, preferably, one week. This treatment is then repeated cyclically.

The following Examples illustrate the invention, but do not limit the scope thereof:

EXAMPLE 1

A transdermal therapeutic system in the form of a plaster for the combined administration of 17β-oestradiol and norethisterone acetate is prepared as follows:

A solution of oestradiol and norethisterone acetate in 95% ethanol is prepared by mixing 0.0430 part by weight of norethisterone-17-acetate and 0.0134 part by weight of oestradiol in 1.000 part by weight of 95% ethanol. The solution is made into a gel by the addition of 0.0188 parts of hydroxypropylcellulose (mol. wt. 1,000,000, Klucel ®) while stirring A contact adhesive is then prepared by mixing polyisobutylene (mol. wt. 1,200,000), polyisobutylene (mol. wt. 35,000) and a light mineral oil in a weight ratio of 1.0:1.27:2.218. This mixture is dissolved in light petrol to give a 35% solution, and an approximately 50 μm thick layer of this contact adhesive solution is poured onto a 75 μm thick foil of silicone-treated polyethylene terephthalate (release liner) and dried at room temperature. The control membrane in the form of a 50 μm thick film of ethylene vinyl acetate copolymer (EVA, 9% vinyl acetate) is laminated to the contact adhesive layer of the resulting two-layered base. The resulting laminate consisting of three layers is cut into pieces of 15×11 cm³. Four portions each of 400 mg of the gelled oestradiol/norethisterone acetate/ethanol mixture are applied to the EVA copolymer side of each piece at regular intervals and, for the backing, a 63.5 μm thick film of polyethylene terephthalate, which may be aluminised, is placed, together with a covering that can be heat-sealed to EVA, over the gel. The backing foil is sealed to the EVA copolymer at the outer edge of each piece at 130° C. under 27 kg. The finished plasters are punched out of the laminate using a punch of 4 cm diameter.

EXAMPLE 2

(a) In vitro tests are carried out to determine the emission of oestradiol and norethisterone acetate from the plasters described above. For this, the basic process of Chandrasekaran, et al., Am. Inst. Chem. Eng. J., 22, 828 (1976) is used. The concentration of norethisterone acetate and of oestradiol in the receptor liquid is determined by chromatography (HPLC).

(b) Results:

| norethisterone acetate: | | |
| --- | --- | --- |
| rate of release [μg/cm² h] | | total quantity released [μg/cm²] |
| 0-24 h | 24-48 h | 0-96 h |
| 2.9 | 3.7 | 182 |

| oestradiol: | | |
| --- | --- | --- |
| rate of release [μg/cm² h] | | total quantity released [μg/cm²] |
| 0-24 h | 24-48 h | 0-96 h |
| 0.17 | 0.23 | 12 |

EXAMPLE 4

The flux of progesterone and synthetic progestrone derivatives is measured in vitro as follows:

In the donor compartment of a diffusion cell according to T. J. Franz, J. Invest. Dermatol. 64, 190-195(1975), a saturated ethanolic solution of the relevant gestagens or the transdermal therapeutic system according to Example 1 is brought into direct contact with the pig skin (approximately 2 cm²) stretched between the donor compartment and the acceptor compartment. After 24 hours, an aliquot of the aqueous acceptor solution from the acceptor compartment is examined for content of the relevant progesterone derivative and, from this, the flux in μg cm²×h is calculated.

| test compound | therapeutically effective daily dose [mg] | | skin permeation in vitro | | necessary surface area of system[1] [cm$^2$] |
| --- | --- | --- | --- | --- | --- |
| | oral | transdermal[1] | alcoholic solution [μg/cm$^2$ · h] | system according Example 1 [μg/cm$^2$ · h] | |
| progesterone | 100–300 | 2 | 3.0 | 0.073 | 1140 |
| norethisterone | 0.5–5 | 0.2 | 0.024 | | 350 |
| medroxyprogesterone acetate | 2.5–10 | 2 | 0.019 | | 4380 |
| d-norgestrel | 0.07–0.15 | 0.05 | 0.028 | | 74 |
| norethisterone acetate | 0.5–5 | 2 | 1.47 | 0.39 | 21 |

[1] estimated values

We claim:

1. A therapeutic system for the transdermal combined administration of oestrogens and gestagens, consisting of:
   (1) a closed outer layer which is impermeable to the constituents of the active ingredient formulation,
   (2) a reservoir containing essential constituents of the active ingredient formulation and a control membrane,
   (3) an adhesive layer and
   (4) a peel-off protective layer on the adhesive layer, characterised in that the therapeutic system contains oestrogen derivative in combination with a synthetic gestagen derivative, and a $C_2$–$C_4$ alkanol as the agent that enhances percutaneous absorption.

2. A therapeutic system according to claim 1, characterised in that the active ingredient formulation contains 17β-oestradiol in combination with norethistereone-17-acetate, and ethanol as the agent that enhances percutaneous absorption.

3. A method of treating climacteric syndrom which comprises applying to a female host a therapeutic system for the transdermal combined administration of oestrogens and gestagens according to claim 1.

* * * * *